United States Patent [19]

Weyl et al.

[11] 4,019,974
[45] Apr. 26, 1977

[54] ELECTROCHEMICAL SENSOR CONSTRUCTION

[75] Inventors: Helmut Weyl, Schwieberdingen; Leo Steinke, Waiblingen-Hegnach, both of Germany

[73] Assignee: Robert Bosch G.m.b.H., Stuttgart, Germany

[22] Filed: Dec. 23, 1975

[21] Appl. No.: 643,934

[30] Foreign Application Priority Data

Feb. 1, 1975 Germany .......................... 2504206

[52] U.S. Cl. ............................. 204/195 S; 204/1 S; 60/276; 123/119 E
[51] Int. Cl.$^2$ ..................................... G01N 27/46
[58] Field of Search ............ 204/1 S, 195 S; 60/276; 123/119 E

[56] References Cited

UNITED STATES PATENTS

| | | | |
|---|---|---|---|
| 3,835,012 | 9/1974 | Hemak | 204/195 S |
| 3,841,987 | 10/1974 | Friese et al. | 204/195 S |
| 3,844,920 | 10/1974 | Burgett et al. | 204/195 S |
| 3,847,778 | 11/1974 | Riddel | 204/195 S |
| 3,891,529 | 6/1975 | Beesch | 123/119 E |

Primary Examiner—T. Tung
Attorney, Agent, or Firm—Flynn & Frishauf

[57] ABSTRACT

To provide for insulation between the conductors of a solid electrolyte ion-conductive oxygen measuring tube and a steel housing thereof, for introduction into the exhaust system of an automotive vehicle, the housing is formed with a shoulder against which a ceramic ring is seated, the tube passing through the ring, and likewise being formed with a shoulder seating against the ring. The outer conductor along the tube extends beyond the ring. A resilient electrically conductive mass such as graphite is packed around the tube, and spaced from the inner walls of the housing by a resilient mass of an insulating powder, such as talcum. The tube is held in position by a second insulating ring, the aperture of which is lined with a metallic sleeve contacting the electrically conductive powder and providing a contact connection to a terminal located in an end insulator secured to the housing; the interior of the tube is likewise connected to another terminal located in the insulator.

17 Claims, 1 Drawing Figure

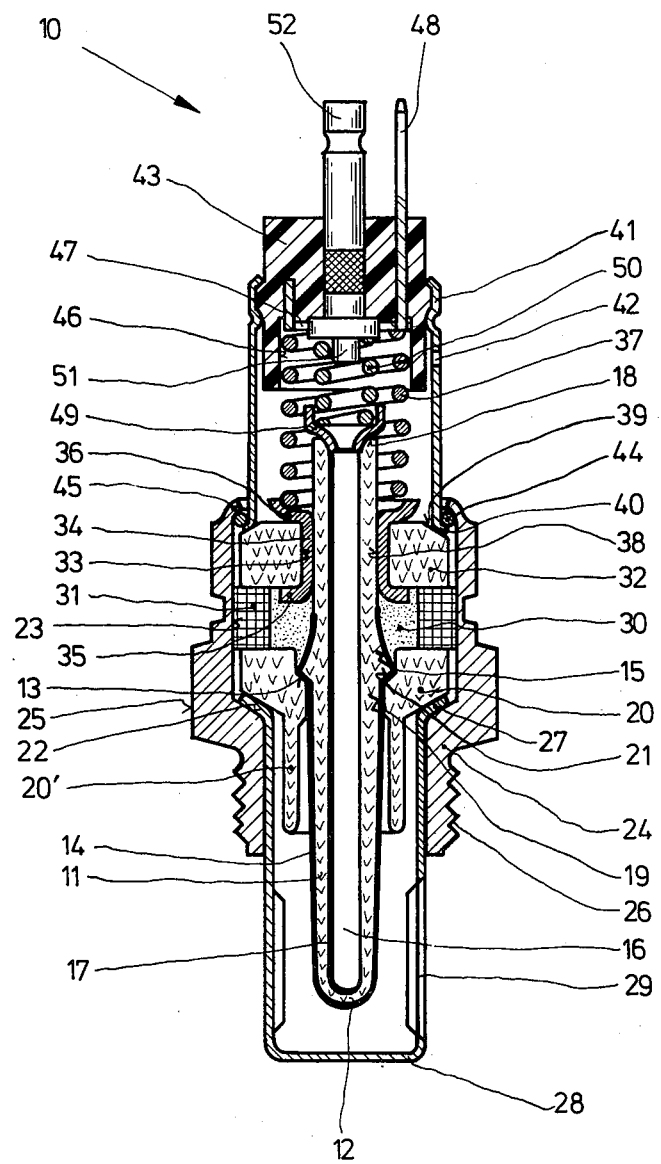

ELECTROCHEMICAL SENSOR CONSTRUCTION

Cross reference to related applications and patents: U.S. Pat. No. 3,841,987, issued Oct. 15, 1974; FRIESE et al; U.S. Pat. No. 3,891,529, Beesch; U.S. Ser. No. 447,475, filed Mar. 4, 1974; POLLNER et al; all assigned to the assignee of the present invention.

The present invention relates to an electrochemical sensor and more particularly to the construction of such a sensor to measure the oxygen content in gases to which the sensor is exposed, especially of exhaust gases in internal combustion engines.

The exhaust gases of internal combustion engines include, inter alia, carbon monoxide, unburned or partially burned hydrocarbons and nitrogen-oxides which all contribute to air pollution. It is necessary to monitor the exhaust products emitted from automotive internal combustion engines in order to decrease air pollution by eliminating as many of the polluting compounds as possible. It is necessary to remove as much of carbon monoxide and unburned hydrocarbons as possible from the exhaust of these engines by converting carbon monoxide and hydrocarbons into their highest oxidation state, that is, in the case of carbon monoxide into carbon dioxide and in the case of hydrocarbons into water, and to convert the nitrogen-oxides into elementary nitrogen.

Removing polluting components from the exhaust of internal combustion engines can be effected by conducting the exhaust gases at a temperature of above 600° C over catalysts, so that the exhaust gases are subjected to a post-combustion. The composition of the exhaust gases must be so arranged, however, that the relationship of air to fuel is approximately stoichiometric. Practically complete conversion to non-polluting compounds is then possible. The stoichiometric relationship between air and fuel is characterized by an air number $\lambda$ of unity ($\lambda = 1$). A $\lambda$-value equal to or less than 1 means that no excess oxygen is present which exceeds the balance condition of the various respective reactions which may take place; a $\lambda$-value greater than 1 means that excess oxygen is present in the mixture; a $\lambda$-value exactly equal to 1 characterizes the state in which the exhaust gas changes from reducing to oxidizing state.

Exhaust gases which are environmentally acceptable, as well as maximum use of fuel being supplied to an engine, that is, best fuel efficiency, require that the $\lambda$-value of the exhaust gases is approximately unity ($\lambda = 1$). Electrochemical sensors are used, exposed to the exhaust gases of the internal combustion engine to be monitored to determine the oxygen content therein. Control systems, responsive to output signals of the sensors, then react to so adjust the relationship of air and fuel being applied to the engine that the air-fuel mixture will have the proper composition which, in turn, affects the exhaust gases emitted from the engine.

The oxygen sensors to which the present invention relates utilize the principle of oxygen ion concentration chains, having ion conductive solid electrolytes. Such sensors are secured in the wall of the exhaust system of the engine. Ambient air is used as a reference for the concentration chain. The solid electrolyte is covered at both sides, at least in part, with an electron conductive layer, such as platinum. The solid electrolyte usually is in the shape of a tube, one end of which is closed; the closed end of the tube extending into the interior of the exhaust system so that the outside surface thereof is exposed to exhaust gases The outer surface, as well as the inner surface of the electrolyte tube are coated, at least in part, with the electron conductive layer. Each electron conductive layer, which may be in strip form, in certain cases, has a contact region with which it is connected to an electrically conductive terminal portion. The terminal portions are usually so arranged that one terminal thereof is formed by the metallic housing with which the sensor is secured in the exhaust pipe system of the internal combustion engine. This terminal, then, is connected to chassis of the vehicle, and the entire chassis body of the vehicle forms one of the conductors from the sensor, usually called the return conductor.

Most vehicles use a multiplicity of electrical loads. The return conductor, then, may have various potentials applied thereto and is practically never completely free of voltage variations. Thus, the output signal as measured across the insulated terminal of the sensor and a random position of the vehicle may not be the output from the sensor itself. The electrical loading characteristics and states of electrical components of the vehicle may therefore change the actual voltage signal to be sensed from the sensor, and thus interfere with proper operation of the control system setting the air-fuel mixture, and, due to the combustion thereof in the engine, interfering with proper composition of the exhaust gases being emitted from the engine.

It is an object of the present invention to provide an electrochemical sensor which is so constructed that its terminals are isolated from the housing of the sensor itself, so that the vehicle chassis will not be used as the return line, but rather has a separate terminal for its own return line; which is sturdy in construction and has a long and reliable life.

SUBJECT MATTER OF THE PRESENT INVENTION

Briefly, the solid electrolyte tube is formed with a shoulder on the outside which engages a first insulating support ring. An electrically conductive sealing mass, such as graphite, is in conductive connection with the electron conductive layer at the outside of the tube; the sealing mass is coaxially surrounded by an electrically insulating sealing mass, to insulate the electrically conductive sealing mass in contact with the outside electron conductor of the tube with respect to the housing. A second insulating ring is placed above the sealing mass, apertured to permit passage of the solid electrolyte tube therethrough. The electrically conductive sealing mass is in contact with a connecting element which leads to one of the terminals of the sensor, located in an insulating end bushing thereof. The contact element preferably is a sleeve surrounding the outside of the tube, made of electrically conductive material, against which a spring can bear, electrically connecting the sleeve to the contact terminal while providing resilient, mechanical connection therewith. The electrical conductor at the interior of the solid electrolyte tube is in electrical contact with a metal bushing which is connected to the other terminal of the sensor, preferably also by means of a compression spring. The arrangement therefore provides electrical contact between the electron conductive layer at the outer surface of the solid electrolyte tube while preventing contct thereof with the housing.

The first insulating ring, the resilient sealing masses, and the second insulating ring, and hence the electrolyte tube, are preferably retained within the housing by means of an offset shoulder in the housing on the one hand and by a peened-over edge of the housing on the other.

The electrically conductive sealing mass is preferably a material which remains elastic, such as graphite; the insulating sealing mass can then be made of an electrically insulating powder, such as talcum. The support or spacer rings are preferably made of ceramic material.

The first insulating support or spacer ring, preferably of ceramic, may have an extended tubular projection partly surrounding, with clearance, the solid electrolyte tube. This greatly extends the creep path between the outer surface of the solid electrolyte and the housing tube. It additionally has the function of a spacer.

The invention will be described by way of example with reference to the accompanying drawing, wherein the single FIGURE is a schematic longitudinal section through a sensor in accordance with the present invention, to an enlarged scale.

The sensor 10 has an ion conductive solid electrolyte tube 11 made of stabilized cubic zirconium dioxide. It is designed to be exposed to exhaust gases of an internal combustion engine by extending into the exhaust gas path thereof. The closed end 12 of the tube 11 forms the end adapted for this exposure. The tube is formed at its outside with a shoulder 13. The outer surface of the solid electrolyte tube has a porous, electron conductive layer 14 of platinum applied thereto at least in part. The platinum layer covers that range of the tube which is exposed to the exhaust gases, and further extends to the shoulder 13 thereof, as well as to a contact region 15 beyond the shoulder. The electron conductive layer 14 then ends, so that the remaining length of the solid electrolyte tube is not coated with platinum, thus saving this expensive material. An electrically insulating glaze is located between the outer surface of the solid electrolyte tube 11 and the electron conductive layer 14 in the region of the shoulder 13 and of the contact range 15. This glaze suppresses decrease of the output voltage signal of the sensor 10. The glaze, being thin, is not shown in the drawings. The electron conductive layer 14 is further coated with a layer of magnesium spinel applied to the layer 14 in the region in which it is exposed to the exhaust gases, to protect the electron conductive layer 14 against mechanical and thermal attack by the exhaust gases.

The solid electrolyte tube 11 has an interior electron conductive path 17 applied at the inner surface 16 thereof. The path 17 reaches down into the closed end 12 and is also made of platinum. This conductive path or track 17 extends at the terminal end of the tube 11 up to the facing edge surface 18 of the solid electrolyte tube 11.

The tube 11 is secured to a housing 24, preferably of steel, which is formed at its outside with a hexagonal surface 25 for engagement with a wrench, and with a thread 26 to securely attach the sensor into the exhaust pipe, or somewhere in the exhaust system of an internal combustion engine. The solid electrolyte tube 11 is secured in the housing this way: A first support and spacer ring 20 is formed with a bore 19 in which the tube 11 is inserted, so that it engages the ring 20 with its shoulder 13 on an abutment 21 formed in the bore 19. To decrease the danger of fracture of the solid electrolyte tube, or of the support ring 20, respectively, a washer made of heat-resistant steel may be located between these two elements. The support ring 20 is electrically insulating, and made of ceramic ($Al_2O_3$) and is indirectly supported on a shoulder 22 in the longitudinal bore 23 of the metal housing 24. The first ring 20 is extended at its lower end into an extension tube 20' which surrounds the solid electrolyte tube 11 with some clearance. The extension is relatively thin-walled and self-cleaning in operation, and functions as a creep barrier. A flange 27 of a protective tube 28 is located between the insulating ceramic ring 20 and the shoulder 22 of the housing. The protective tube 28 surrounds the solid electrolyte tube 11 in the region where it extends into the exhaust gases. It is formed with openings 29 to permit ingress of the exhaust gases. The tubular extension 20' of the first support ring 20 is spaced from the interior surface of the protective tube 28 and thus further increases the creep current path between the electron conductive layer 14 of the solid electrolyte tube 11 and the protective tube 28 which, due to its engagement with the housing 24, is connected to ground or chassis of the motor vehicle. An electrically conductive sealing mass 30, consisting of graphite, is located above the first insulating ring 20 in the bore 23 of the housing 24. The mass 30 surrounds the electron conductive layer 14 in the contact region 15 thereof. It, in turn, is coaxially surrounded by an electrically insulating sealing mass 31. The sealing mass 31 consists of talcum powder. The sealing mass 30, as well as the sealing mass 31, are held in position by an electrically insulated second ring 32, likewise made of ceramic material, and inserted in the bore 23 of the housing. The second ring 32 has a central opening 33 through which the solid electrolyte tube passes. An electrically conductive sleeve 34 is slipped over the solid electrolyte tube 11. Sleeve 34 is flanged at both its ends to form flanges 35, 36. Flange 35 of sleeve 34 extends into the sealing mass 30 and thus is in electrical contact therewith; flange 36 is shaped to form a guide cup for a compression spring 37. The sleeve 34 fills the gap between the solid electrolyte tube 11 and the opening or bore 33 in the second ring 32. The solid electrolyte tube 11 is thus supported within the inner opening 38 of the sleeve 34, so that the end portion of the solid electrolyte tube 11 is securely held and guided thereby.

The second ring 32 is formed with a shoulder 39 at its outer circumference. A flange 40 of a protective sleeve 41, made of sheet metal and formed with openings 42 for ingress of air, is seated on shoulder 39. A cylindrical insulating stopper 43 is seated in the end portion of sleeve 41, held therein by clamped, peened or otherwise deformed surface regions, as well known, and for example as illustrated in the drawing. The flange 40 of the sleeve 41 is externally expanded. It is held in position by a ring bushing or washer 44 which in turn is compressed by a peened-over edge 45 of the housing 24, thus securely holding the entire assembly together.

The compression spring 37, seated against the cup-shaped flange 36 of sleeve 34, is made of electrically conductive material. It is laterally held in position in a cup-shaped enlargement 46 formed in the insulating stopper 43. In longitudinal direction, the spring is compressed. Spring 37 engages an electrically conductive inturned leg 47 molded, for example, into the stopper 43 and carried therethrough and forming one of the terminals 48 of the sensor.

The interior conductor 17 of the solid electrolyte tube 11 is connected to the second terminal 52 thereof. The end surface 18 of the solid electrolyte tube 11 is engaged by a contact ring or bushing 49 which is in electrical contact with the interior conductor 17, and additionally forms a guide cup for the contact spring 50. Contact spring 50 is longitudinally biassed and engages with its other end a pin 51 forming an extension of the second terminal 52, likewise carried through and preferably sealed or molded into the insulating stopper 43. The contact spring 50, a spiral spring like spring 37, is coaxial thereto and located in the interior thereof, with sufficient clearance to prevent contact therebetween, and to provide for electrical isolation. A plastic sleeve may also be inserted between the springs, for example seated on the extension of the tube 11 to additionally separate the two springs from each other.

The sensor thus provides for complete electrical isolation of the solid electrolyte tube from the housing secured into the exhaust system of the internal combustion engine. The conductor 17 applied to the inner surface 16 of the electrolyte tube 11 is connected by means of the contact cup 49 and spring 50 to the contact 52; the electron conductive layer 14 at the outside of the tube 11 is out of contact with the housing 24, connected to terminal 48 in the insulating stopper 43 through the sealing mass 30, sleeve 34 and compressiom spring 37.

The compression springs are not strictly necessary, and other contacting arrangements between the conductor 17 and the terminal 52 can be used, preferably utilizing the contact spring 50, however.

Various changes and modifications may be made within the scope of the inventive concept.

We claim:
1. Electrochemical sensor construction to determine the oxygen content of gases having a solid electrolyte tube (11) closed at one end (12);
   an electron conductive porous layer (14) at the outside of the tube covering at least part of the surface exposed to the gases;
   a first connecting terminal (48) in electrically conductive connection with the conductive layer (14);
   an inner conductor (17) on the inside of the tube, and in contact with the inside surface thereof;
   a second connecting terminal (52) in electrically conductive connection with the inner conductor (17);
   an electrically conductive housing (24, 41) concentrically surrounding the tube and formed to permit ingress of air interiorly of the tube while exposing the outside thereof to the gases, and retaining said terminals in insulated relation with respect thereto;
   wherein the solid electrolyte tube (11) is formed with a shoulder (13);
   a first electrically insulating spacer ring (20) spacing the shoulder from the housing (24);
   a conductive resilient sealing mass (30) in contact with the conductive layer (14) of the solid electrolyte tube (11);
   an insulating sealing mass (31) surrounding the conductive sealing mass (30) and spacing the conductive sealing mass (30) from the housing (24, 41) to electrically insulate the conductive sealing mass, and hence the conductive layer (14) with respect to the housing;
   a conductive element (34) surrounding the tube and bearing against the electrically conductive sealing mass (30);
   first conductive means (37) contacting the conductive element (34) and the first terminal (48);
   second conductive means (50) in contact with the inner conductor (17) in the interior of the tube and the second terminal (52);
   and an insulating terminal block (43) closing off the housing (24, 41), the connecting terminals (48, 52) being secured in and passing through said terminal block to provide electrically and mechanically accessible terminals to the conductive layer (14) and the second conductor (17) and to electrically insulate the tube, and its terminals from the housing (24, 41).

2. Sensor according to claim 1, further comprising a second electrically insulating spacer ring (32) having an aperture (33) and surrounding the outside of the solid electrolyte tube (11), the insulating sealing mass (31) and the conductive sealing mass (30) being located between and bearing against said first sealing ring (20) and said second insulating spacer ring (32), and said conductive element (34).

3. Sensor according to claim 2, wherein the electrically conductive element (34) is a sleeve extending through the aperture of the second electrically insulating ring (32) and essentially filling a gap formed between the aperture (33) of the second insulating ring (32) and the outside of the solid electrolyte tube, said sleeve being in electrical contact with the electrically conductive sealing mass (30) and the first conductive means (37), and hence with the first terminal (48).

4. Sensor according to claim 3, wherein the housing (24) is formed with an interior shoulder (22) retaining the first ring (20), the sealing masses (30, 31) and the second ring (32), the sleeve (34), and hence the solid electrolyte tube (11) being thus indirectly seated on the shoulder;
   and a rolled-over edge of the housing (45) holding the second ring (32) in position.

5. Sensor according to claim 3, wherein at least one of said insulating rings comprises a ceramic material.

6. Sensor according to claim 3, wherein the first conductive means comprises an electrically conductive compression spring (37) engaging the sleeve (34) with one end thereof, the other end of the compression spring being in electrical contact with the first terminal (48).

7. Sensor according to claim 3, wherein the second electrically conductive means comprises a compression spring (50) and a spring cup (49) of electrically conductive material and in electrical contact with the inner conductor (17) of the solid electrolyte tube (11) with one end thereof, the other end of said spring (50) being in electrically conductive connection with the second terminal (52).

8. Sensor according to claim 1, wherein the conductive element (34) comprises an apertured sleeve surrounding the tube (11) and bearing against the electrically conductive sealing mass (30), the electrolyte tube (11) extending through the aperture thereof.

9. Sensor according to claim 1, wherein the electrically conductive sealing mass (30) comprises elastic material.

10. Sensor according to claim 1, wherein the electrically conductive sealing mass (30) comprises graphite.

11. Sensor according to claim 1, wherein the electrically insulating sealing mass (31) comprises an electrically insulating powder.

12. Sensor according to claim 11, wherein the powder (31) is talcum.

13. Sensor according to claim 1, wherein the spacer ring comprises ceramic.

14. Sensor according to claim 1, wherein the first insulating ring (20) is formed with a tubular extension (20') surrounding the solid electrolyte tube (11) with clearance, and extending into the housing with clearance from the inner wall of the housing, to provide for an extended creep path.

15. Sensor according to claim 1, wherein the insulating terminal block comprises an electrically insulating stopper (43) closing off the end of the housing, both said terminals (48, 52) being molded in said insulating stopper (43).

16. Automotive type electrochemical sensor construction to determine the oxygen content of gases having
- a solid electrolyte tube (11) closed at one end (12);
- an electron conductive porous layer (14) at the outside of the tube covering at least part of the surface exposed to the gases;
- an inner conductor (17) on the inside of the tube and in contact with the inside surface thereof;
- a metallic, electrically conductive housing (24, 41) concentrically surrounding the tube and formed to permit ingress of air interiorly of the tube while exposing the outside thereof to the exhaust gases;
- insulating means (20, 31, 32) located between the housing (24, 41) and the outside of the tube (11) retaining said tube in the housing while insulating the tube from the housing;
- an insulating terminal block (43) secured to the housing;
- first electrically conductive means (31, 32, 37) in electrically conductive relation to said electrically conductive layer;
- a first connecting terminal (48) secured in and passing through said terminal block (43) having an attachment end outside of the housing and a terminal end inside of the housing, the terminal inside of the housing being connected in electrically conductive connection to said first electrically conductive means;
- second electrically conductive means (49, 50) in electrically conductive connection with the inner conductor (17) of the solid electrolyte tube;
- and a second connecting terminal (52) having an externally accessible terminal end and an internal terminal end, passing through and being secured to said terminal block (43) and connected in electrically conductive connection with said second electrically conductive means
- to insulate the solid electrolyte tube (11) from the housing and to provide externally accessible electrical terminals electrically insulated from the housing and electrically separate with respect thereto.

17. Sensor construction according to claim 16, wherein at least part of said electrically conductive means comprises resiliently compressive means (30, 37, 50) to resiliently support the solid electrolyte tube in the housing.

* * * * *